United States Patent [19]

Senni et al.

[11] 4,314,940
[45] Feb. 9, 1982

[54] METHOD FOR THE PURIFICATION OF RAW CAPROLACTAM

[75] Inventors: Paolo Senni; Nando Toderi, both of Colleferro, Italy

[73] Assignee: SNIA Viscosa Societa' Nazionale Industria Applicazioni Viscosa S.p.A., Milan, Italy

[21] Appl. No.: 142,860

[22] Filed: Apr. 21, 1980

[30] Foreign Application Priority Data

Apr. 30, 1979 [IT] Italy ............................. 22250 A/79

[51] Int. Cl.³ ........................................ C07D 201/16
[52] U.S. Cl. ............................................. 260/239.3 A
[58] Field of Search ................................. 260/239.3 A

[56] References Cited

U.S. PATENT DOCUMENTS 4,013,640  3/1977  Somekh ..................... 260/239.3 A Primary Examiner—Robert T. Bond Attorney, Agent, or Firm—Hubbell, Cohen, Stiefel & Gross

[57] ABSTRACT

A method for the purification of raw caprolactam containing primary amides of the formula

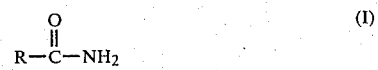

wherein R is a hydrocarbon radical having 1–14 carbon atoms is described. The raw caprolactam is treated with at least one compound containing at least one hydroxyl group, in an amount of at least 20% by weight with respect to the raw caprolactam, at a temperature equal to or higher than that at which the ammonia, which is a part of the amide of formula I, is liberated. The caprolactam is then separated and isolated from the hydroxyl containing compound by known methods.

10 Claims, No Drawings

METHOD FOR THE PURIFICATION OF RAW CAPROLACTAM

BACKGROUND OF THE INVENTION a. Field of the Invention

The present invention relates to a method for the purification of raw caprolactam containing, as impurities, one or more primary amides having the formula I

wherein R is a hydrocarbon radical having from 1 to 14 carbon atoms, in particular hexahydrobenzamide.

b. Prior Art

Methods for purifying caprolactam from the amides which it contains are known. Said methods may be grouped in two different classes, chemical and physical methods. Thus, e.g., a chemical method is claimed in the Japanese patent application No. 46-23751, and is characterized by the fact that raw caprolactam is treated with a solution of sodium hypochlorite. Another chemical method is claimed in DOS No. 1.926.932 and consists in treating the molten raw caprolactam with metal oxides. The physical methods mainly consist in distilling and/or rectifying the caprolactam. Thus e.g. in English Pat. No. 1,157,416 a method is described for purifying caprolactam by distillation. In Italian patent application No. 20612 A/79 of the Applicant a method is described for purifying raw caprolactam by combination of distillation and rectification operations.

The aforesaid hitherto known chemical and physical methods for the purification of caprolactam have, however, considerable disadvantages. Thus e.g., the chemical purification methods have the disadvantage that they are not selective, inasmuch as besides the amides of formula I, the caprolactam too may react for example with the hypochlorite, whereby new products such as chlorolactam are formed, from which the caprolactam can be separated and isolated only with difficulty.

The disadvantages of the known physical methods may be summed up in the fact that it is difficult, in the purification of caprolactam by rectification, quantitatively to separate two products having boiling points close to one another, unless a rectification column having a very high number of plates is used.

In general there is a tendency to collect or separate one of the two products in the purest possible form to leave a part of the other product mixed with the first and to discharge the mixture as heads or tails of the distillation. When, as in the case of caprolactam, the compound to be purified is sensitive to heat, the use of a very large number of plates or high reflux ratios may cause the distruction of a part of the product or secondary reactions such as polymerization, which is very harmful because it causes the loss of yield and makes the operation of the apparatus difficult.

In the purification of caprolactam by rectification, as disclosed in Italian patent application No. 20612 A/79, the highest boiling amides of formula I, in particular hexahydrobenzamide, concentrate in the distillation tails, always however together with part of the caprolactam. The resulting residue therefore always contains a large amount of caprolactam which must be subsequently recovered to render the processes economical.

Italian patent application No. 20612 A/79 contains the following disclosure:

"This invention relates to a method of purifying caprolactame, e.g. caprolactame of the same grade as yielded by reacting nitrosyl compounds with carbocyclic derivatives.

It is a well known fact that the aforesaid reaction yields, additionally to caprolactame, small amounts of non-cyclic amides, such as acetamide, popionamide, butyramide, n-valeramide, benzamide, tetrahydrobenzamide, hexahydrobenzamide, and morever, still in small amounts, aliphatic and aromatic cyclocarboxylic acids, epsilon-aminocaproic acid, and unsaturated oxidable substances.

Several methods of purifying caprolactame are known in the art. Thus, for example, when effectuated by reacting nitrosyl compounds with carbocyclic derivatives, the purification of caprolactame (following its extraction from the sulphuric reaction mass and known steps for separating raw caprolactame) is substantially carried out, according to current practice, by means of two separate and discrete chemical treatments, a first one directed to destroying the amides, and a second one directed to reducing or eliminating the easily oxidable substances. More specifically, these treatments consist of subjecting firstly the raw caprolactame to the action of sodium hypochlorite (conversion of the amides into more volatile amines), and subsequently to an oxidizing action, e.g. with potassium permanganate or ozone (decomposition of the oxidable substances); the product, after undergoing that treatment, is subjected to distillations, possibly under vacuum conditions, without rectification, thereby a "polymerization grade" caprolactame is obtained. Said chemical treatments, however, have the following drawbacks:

(1) they are expensive;
(2) they yield impurities of a different nature (such as chloro-lactames, for instance) which, although only some ppm, result in contamination of the caprolactame;
(3) the treatments with hypochlorite-permanganate, respectively hypochlorite-ozone, are not absolutely selective, even when the very high caprolactame-byproducts ratio is taken into account, thereby part of the caprolactame is destroyed by these chemicals, with an attendant appreciable decrease of the yield.

The applicant has now surprisingly found a method of purifying caprolactame by the application of only one line of physical purification. With this process it becomes possible to obtain a caprolactame of a purity even higher than that obtainable with the use of hypochlorite-permanganate, respectively hypochlorite-ozone.

By not applying said treatments of a chemical nature, not only all of the aforesaid disadvantages are eliminated, but a lower cost and improved environmental protection can also be achieved in the purification process.

This invention sets out to provide a caprolactame purification process by vacuum distillation, characterized in that said distillation is carried out, in a continuous and/or discontinuous (batch distillation) manner, in the following stages or steps, in the same order as listed herebelow:

(a) fast vacuum distillation of the raw caprolactame, possibly in the presence of an alkaline and/or alkaline-earth hydroxide;

(b) distillation with vacuum rectification of the caprolactame yielded as distillate from (a), with separation from the high-boiling, and possibly low-boiling, byproducts; and (c) fast vacuum distillation of the caprolactame yielded from (b), in the presence of an alkaline and/or alkaline-earth hydroxide.

The term "fast distillation", as used herein, is intended to describe an operation wherein the evaporated material is no more recycled, in any substantial manner, into the evaporation zone. The percentage by weight of the alkaline or alkaline-earth hydroxide, at step (c), and possibly (a) as well, with respect to caprolactame, varies preferably in the 0.05% to 5% range, and more preferably from 0.1% to 1.0%.

Advantageously, the temperature of the various steps (a), (b) and (c) are preferably maintained within the following limits:
Step (a)—100° to 150° C.
Step (b)—vapors, 110° to 150° C.; reboiler, 120° to 180° C.;
Step (c)—100° to 150° C.

As the alkaline hydroxide, potassium hydroxide is used of preference, and more preferably sodium hydroxide, whereas when an alkaline-earth hydroxide is used, calcium hydroxide is preferred; however, as the hydroxide, according to this invention, sodium hydroxide is still more preferably employed. Said alkaline or alkaline-earth hydroxides are preferably employed, in accordance with this invention, in the form of a solution, and more preferably of an acqueous solution.

According to a variant of the invention, (mainly suggested by economics and physical-mechanical considerations) the purification of caprolactame is carried out at the steps (a), (b) and (c) such as to obtain:

From Step (a), a distilled portion corresponding to 90–98% by weight with respect to the raw caprolactame, and 2–10% by weight of residue, again with respect to the raw caprolactame;

From Step (b), a head fraction, corresponding to 2–5% by weight with respect to the caprolactame supplied from Step (a), a core fraction, corresponding approximately to 90% by weight of the caprolactame supplied from Step (a), and a residue corresponding to 5–8% by weight again with respect to the caprolactame supplied from Step (a);

From Step (c), a fast distillate to yield a residue corresponding to approximately 5–10% by weight of the caprolactame supplied from Step (b).

In step (b), the head fraction may or may not be separated from the caprolactame which is supplied to the successive step (c).

The operating conditions which can be adopted for the two fast distillations, as per steps (a) and (c), are the following:
Temperatures in the 125° to 130° C. range;
Residual pressure, 4 mm Hg; and for the rectification of step (b):
Head temperatures in the 105° to 110° C. range;
Reboiler temperature in the 120° to 165° C. range.

The finally yielded caprolactame has the following characteristics:
Volatile bases, 0.1 meq/kg;
Permanganate Number, 15,000 seconds;
HAZEN color, less than 5;
Absorption at 290 nm, 0.008;
Absorption summation from 260 to 300 nm, 0.290.

None of the individual operations, when carried out separately and/or in a different order from the one provided by the invention, yields caprolactame having the aforesaid characteristics.

A further object of this invention includes the purified caprolactame as obtained with the purification method described hereinabove.

The following example should be considered as merely illustrative and in no way limitative of this invention.

EXAMPLE

Step (a)

Into a glass flask equipped with thermometer, capillary tube for the introduction of nitrogen, vapor collecting and condensing system, vacuum unit, and vacuum measuring gauges, as well as outer electric heater, there are charged 100 parts by weight of raw caprolactame and 0.3 parts by weight of NaOH, as a 50% solution in $H_2O$. The flask is treated up to 110° C. at a residual pressure of 1.2 mm Hg. The results are shown in the following Table 1.

TABLE 1

| CHARGE | 100 parts by weight |
|---|---|
| Total volatile bases charged | 24.3 meq/kg |
| Volatile bases charged as hexahydrobenzamide (HBA) | 17.8 meq/kg |
| Permanganate Number | 0 seconds |
| DISTILLATE | 80 parts by weight |
| Total volatile bases | 10.2 meq/kg |
| HBA volatile bases | 7.4 meq/kg |
| Permanganate Number | 150 seconds |
| TAILS | 20 parts by weight |
| Total volatile bases | 80.7 meq/kg |
| HBA volatile bases | 59.4 meq/kg |
| Permanganate Number | 0 seconds |
| Oligomers | none |

Step (b)

The apparatus utilized to carry out step (b) comprises a glass flask equipped with capillary tube for the introduction of nitrogen, thermometer, pressure gauge for measuring the vacuum, and outer electric heater system. Over the flask, there is mounted a 20-plate rectification column which is connected to a reflux head and then to an overall condenser discharging into a distillate collection flask whereto a vacuum is applied. Into the heated flask, are charged 80 parts by weight of caprolactame from the distillate of step (a); heat is applied after a 3 mm Hg vacuum has been created in the collecting flask (in the boiler the vacuum is of 25 mm Hg). Before the collection is initiated, the caprolactame is fully recycled to ensure that the column operating conditions are achieved. Then, 4 parts by weight of caprolactame are distilled, collected and separated at the head temperature of 124° C., and 64 parts by weight of caprolactame are collected and separated at the temperature of 125° C. Distillation is then discontinued, and in the boiler there remain 12 parts by weight of caprolactame. The results obtained are tabulated in the following Table 2.

TABLE 2

| CHARGE | 80 parts by weight |
|---|---|
| RECTIFICATION HEADS | 4 parts by weight |
| Total volatile bases | 1.78 meq/kg |
| HBA volatile bases | none |
| Permanganate Number | 0 seconds |

TABLE 2-continued

| RECTIFICATION TAILS | 12 parts by weight |
|---|---|
| Total volatile bases | 66.5 meq/kg |
| HBA volatile bases | 49.3 meq/kg |
| Permanganate Number | 0 seconds |
| Oligomers | none |
| RECTIFICATION CORE | 64 parts by weight |
| Total volatile bases | 0.17 meq/kg |
| HBA volatile bases | none |
| Permanganate Number | 3800 seconds |

Step (c)

The apparatus employed to carry out this step is the same as for step (a). There are charged into it 64 parts by weight of caprolactame from the rectification core (step (b)) and 0.15 parts by weight of NaOH as a 50% solution in $H_2O$. One proceeds as in step (a), and the results are tabulated in the following Table 3.

TABLE 3

| CHARGE | 64 parts by weight |
|---|---|
| TAILS | 6.4 parts by weight |
| Total volatile bases | 0.76 meq/kg |
| Permanganate Number | 0 seconds |
| Oligomers | none |
| DISTILLATE | 57.6 parts by weight |
| Total volatile bases | 0.04 meq/kg |
| HBA volatile bases | none |
| Permanganate Number | 15,000 |
| Absorption at 290 nm | 0.008" |

Still, the physical methods for the purification of caprolactam, according to the known art, are generally more advantageous than the chemical methods inasmuch as they do not form new by-products and do not consume reagents, provided that all or nearly all the caprolactam can be recovered.

SUMMARY OF THE INVENTION

The Applicant has now surprisingly found that it is possible to purify raw caprolactam from impurities comprising amides according to formula I—by treatment of the raw caprolactam with an hydroxylated compound at a temperature at which the amides according to formula I are decomposed with the evolution of ammonia.

An object of the present invention is therefore a method for the purification of raw caprolactam containing one or more amides having the general formula I, characterized by the fact that said raw caprolactam is treated with at least one compound containing at least one hydroxyl group, in an amount of at least 20% by weight with respect to the raw caprolactam, at a temperature equal to or higher than that at which the amides according to formula I are decomposed with the evolution of ammonia, the caprolactam being subsequently separated and isolated from said hydroxyl containing compound and from the reaction products of said compound with the amides, by known methods, such as e.g. those described in Italian Pat. No. 956.941 of the applicant.

DETAILED DESCRIPTION OF THE PREFERRED EMBODIMENTS

According to the present invention, either an aliphatic compound or an aromatic compound, such as mono- or poly-functional aliphatic or aromatic alcohols, or phenols, may be employed as compounds containing at least one hydroxyl group. Preferably a phenol is employed as the compound containing a hydroxyl group, and more preferably a phenol which contains as a substituent at least one alkyl group, more preferably a branched group, such as ortho-tertiary butylphenol.

According to the present invention raw caprolactam is preferably treated with the compound containing at least an hydroxyl group at a temperature comprised between 100° and 350° C., and more preferably between 220° and 320° C., the reaction time of said treatment being suitably chosen in the range from 10 minutes to 10 hours, preferably from 1 hour to 5 hours.

The weight ratio of the compound containing at least an hydroxyl group to the raw caprolactam preferably varies, according to the present invention, from 20:1 to 0.2:1, and more preferably between 10:1 and 1:1; the most preferred ratio being between about 7:1 and 2:1. The presence of said hydroxylated compound and the particular weight ratios used are necessary and indispensable for preserving the caprolactam from the polymerization reaction, which produces oligomers and therefore caprolactam losses, even if the temperature and treatment time are high and fall within limits wherein the caprolactam polymerizes in the absence of the aforesaid compounds.

According to the present invention, the reaction between the raw caprolactam and the compound containing at least one hydroxyl group may be effected at room pressure and under pressure in such a way as to maintain the reacting system liquid.

For example, when low boiling hydroxylated compounds and relatively high temperature are used, it is convenient to operate at a pressure higher than room pressure, whereas with high boiling hydroxylated compounds it is convenient to operate at room pressure.

After the amide or the amides of formula I have been decomposed, according to the present invention, with the liberation of ammonia, the caprolactam may be separated and isolated from the hydroxylated compound by known methods, e.g. as described in Italian Pat. No. 956.941.

The method for the purification of raw caprolactam which contains amides, according to the present invention, may be applied with particular success by treating with the hydroxylated compound the tails obtained in the rectification of caprolactam according to the process claimed in Italian patent application No. 20612 A/79, said tails containing high concentrations of linear amides.

In order to accelerate the decomposition of the amides of the formula I and to permit said decomposition to be as complete as possible, it is convenient continuously or discontinuously to remove the ammonia which forms as a result of the decomposition. This can be done by bubbling through the reaction mass or passing over the surface of said mass a stream of an inert gas, such as e.g. nitrogen.

According to a variant of the present invention, the reaction is carried out in glass or steel vessels provided with heating means, wherein there is charged the caprolactam which contains the amide or the amides of formula I, e.g. caprolactam which contains hexahydrobenzamide, and the compound containing at least one hydroxyl group, e.g. o-tertiary butylphenol. The vessel is then closed and a moderate nitrogen stream is passed through. The gas which flows out of the apparatus wherein the treatment has been carried out, which contains nitrogen and ammonia, is conveyed into a vessel which contains diluted sulphuric acid and is titrated so as to collect and measure the liberated ammonia. The vessel is then heated and maintained at the temperature of 290° C. for 2 hours. The vessel is then cooled and the residual content of amides of formula I is determined by conventional methods, e.g. by gas chromatography or by the method for the determination of volatile bases which consists in boiling a weighed sample of the product with sodium hydroxide and water and in collecting and titrating the ammonia which develops, a method very well known to persons skilled in the art. The caprolactam is then separated from the compound which contains the hydroxyl group, by known methods, e.g. by addition of cyclohexane and subsequent extraction with water.

The decomposition of the amides according to the formula I may be effected, according to the invention, both continuously and discontinuously. In the discontinuous process the tails of caprolactam rectification are conveniently treated in the way hereinbefore described, in order subsequently to recover the caprolactam which is present in said tails. In the continuous process, the tails of a rectification are conveniently treated in the way described and then continuously conveyed to a caprolactam extraction treatment e.g. the treatment described in Italian Pat. No. 956941.

A further object of the present invention is the caprolactam purified by the method according to the invention.

The following examples are illustrative but are not intended to limit the scope of the present invention.

The indicated percentage of reacted amide is determined by gas chromatography for the sake of a convenient and rapid analysis.

EXAMPLE 1 g 14.585 of caprolactam which contains g 0.415 (0.83%) of hexahydrobenzamide and g 35 of orthotertiary butylphenol, are charged into a steel vessel having a gastight lid provided with a thermocouple for measuring the temperature and nitrogen inlet and outlet pipes. The vessel is closed and is heated to 290° C. while maintaining within it a pressure of 3 atmospheres and a nitrogen flow, referred under normal conditions, of 17.5 lt/h. After two hours the autoclave is cooled, the pressure is released and the product is discharged. During the reaction the ammonia which is contained in the nitrogen and which flows out of the vessel wherein the caprolactam is treated with the hydroxylated compound, is determined. It is found that after two hours the amount of ammonia which is present in the nitrogen is very low, which indicates that the reaction nears completion.

From the gas chromatographic analysis of the discharged solution a content of 29.6% of caprolactam and 0.15% of hexahydrobenzamide is determined. The decomposition of the amide is found to be 82%.

EXAMPLES 2 TO 4

By using the apparatus and the same reagents as described in Example 1, but operating at variable temperatures and times, the following results are obtained:

| Example n° | Reaction temperature °C. | Reaction time hours | Hexahydrobenzamide present | | |
|---|---|---|---|---|---|
| | | | In the discharged charged caprolactam (% by weight) | In the charged caprolactam (% by weight) | In the discharged caprolactam (% referred to the amount charged) |
| 2 | 310 | 0.5 | 0.83 | 0.40 | 48.2 |
| 3 | 310 | 1.0 | 0.83 | 0.13 | 15.7 |
| 4 | 310 | 2.0 | 0.83 | traces | about 0 |

We claim:

1. A method for the purification of raw caprolactam which contains as impurities one or more primary amides having the formula I

wherein R is a hydrocarbon radical having from 1 to 14 carbon atoms, comprising, treating said raw caprolactam with at least one compound Y containing at least one hydroxyl group, said compound being a mono- or polyfunctional aliphatic or aromatic alcohol or phenol, in an amount of at least 20% by weight with respect to the raw caprolactam, at a temperature equal to or higher than that at which said primary amide of Formula I reacts with compound Y to form ammonia, maintaining said temperature for a sufficient time for said reaction to near completion; and separating said caprolactam.

2. Method according to claim 1, wherein the weight ratio of the compound Y and the raw caprolactam is between 20:1 and 0.2:1.

3. A method according to claim 2, wherein said weight ratio is maintained between about 7:1 and 2:1 by weight.

4. A method according to any one of claims 1, 2 or 3, wherein compound Y is a phenol.

5. A method according to claim 4, wherein said phenol has at least an alkyl group containing from 1 to 5 carbon atoms as a substituent.

6. A method according to claim 5, wherein the phenol contains a branched alkyl group as a substituent.

7. A method according to claim 6, wherein orthotertiary butylphenol is used as the phenol.

8. A method according to any one of claims, 1, 2, or 3 wherein the raw caprolactam is contacted with the compound Y at a temperature between 100° C. and 350° C.

9. The method according to claim 1 wherein weight ratio of the compound Y and the raw caprolactam is between 10:1 and 1:1 by weight.

10. The method according to claim 8 wherein the temperature is between 220° C. and 320° C.

* * * * *